United States Patent

Kricsfalussy et al.

[11] Patent Number: 5,523,452
[45] Date of Patent: Jun. 4, 1996

[54] PROCESS FOR PREPARING DIMETHYL CARBONATE

[75] Inventors: Zoltan Kricsfalussy; Heinrich Steude; Helmut Waldmann; Kaspar Hallenberger, all of Leverkusen; Wolfram Wagner, Dormagen; Hans-Joachim Traenckner, Leverkusen, all of Germany

[73] Assignee: Bayer Aktiengesellschaft, Leverkusen, Germany

[21] Appl. No.: 358,133

[22] Filed: Dec. 16, 1994

[30] Foreign Application Priority Data

Dec. 23, 1993 [DE] Germany ............... 43 44 159.9

[51] Int. Cl.⁶ ................................. C07C 68/00
[52] U.S. Cl. ................................. 558/277
[58] Field of Search ....................... 558/277

[56] References Cited

U.S. PATENT DOCUMENTS

| | | |
|---|---|---|
| 3,846,468 | 11/1974 | Perrotti et al. |
| 4,218,391 | 8/1980 | Romano et al. |
| 5,142,087 | 8/1992 | Joerg et al. |
| 5,233,072 | 8/1993 | Kricsfalussy et al. |
| 5,274,163 | 12/1993 | Rechner et al. ............ 558/277 |

FOREIGN PATENT DOCUMENTS

| | | |
|---|---|---|
| 0413215 | 2/1991 | European Pat. Off. |
| 2110194 | 11/1971 | Germany. |
| 2743690 | 4/1978 | Germany. |
| 4138755 | 5/1993 | Germany. |
| 4325651 | 2/1995 | Germany. |

OTHER PUBLICATIONS

Chemical Abstracts, vol. 73, 1970, p. 312; CA#14236a: "Dialkyl and diaryl carbonates", J. Tsuji et al.

Bayer's Patent Application (Le A 29 848), 18 pages; "Process for the preparation of dialkyl carbonates"; DE 4,325, 651, published Feb. 2, 1995.

*Primary Examiner*—Johann Richter
*Assistant Examiner*—Michael G. Ambrose
*Attorney, Agent, or Firm*—William C. Gerstenzang; Sprung Horn Kramer & Woods

[57] ABSTRACT

The preparation of dimethyl carbonate by reaction of methanol, carbon monoxide and oxygen in the presence of Cu compounds is carried out in distillation units and the water of reaction is removed at least partially from the stripping region or the bottom phase.

9 Claims, 2 Drawing Sheets

PROCESS FOR PREPARING DIMETHYL CARBONATE

BACKGROUND OF THE INVENTION

1. Field of the Invention

The invention relates to an improved process for preparing dimethyl carbonate (DMC) by oxycarbonylation of methanol in the presence of Cu salts.

Dimethyl carbonate is an intermediate having low toxicity and can replace toxic intermediates, such as phosgene or dimethyl sulphate, in many reactions. Furthermore, it is not corrosive. Its use gives no environmentally damaging by-products.

Examples of such reactions of dimethyl carbonate are the preparation of urethanes from aliphatic or aromatic amines, which in turn can be cleaved to give the corresponding isocyanates. Dimethyl carbonate can, for example, also replace dimethyl sulphate in the quaternization of amines or in the methylation of phenol or of naphthols. Dimethyl carbonate can also be added to motor vehicle fuel to improve the octane number, e.g. in place of lead compounds. This importance of dimethyl carbonate has prompted the search for a technically simple and environmentally friendly production process which is suitable for large capacities without significant by-product formation or coupled material circuits.

2. Description of the Related Art

To prepare dimethyl carbonate, there are various preparative processes which have been tested on a small scale and also industrially. The preparative routes which are based on the catalytic reaction of methanol with carbon monoxide and oxygen in accordance with the following equation have been intensively studied by various groups of workers:

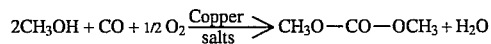

$$2 CH_3OH + CO + 1/2\, O_2 \xrightarrow{\text{Copper salts}} CH_3O-CO-OCH_3 + H_2O$$

The copper compounds acting as catalysts have thus been used in the form of various copper salts. Use of copper(II) chloride as catalyst in accordance with JP-45/11129 (1970) gives unsatisfactory selectivities. Particular problems are caused by the formation of relatively large amounts of methyl chloride which, because of its high volatility, tends to distribute itself ubiquitously throughout the entire production plant and can lead to corrosion in virtually the whole plant.

Better selectivities are obtained by using organic complexing agents (DE-A 21 10 194), but this gives the problem of separating off the catalyst salts which are partially dissolved in the reaction mixture, but the major part of which is present as a suspension.

Particularly problematical is carrying out this reaction in accordance with DE-A 27 43 690, since the catalyst salts in the reaction mixture are virtually completely undissolved, but are merely suspended. These salts have to be conveyed through the reaction zone and through the cooling equipment and after the reaction have to be separated off mechanically, e.g. by means of centrifuges. Besides the corrosion already mentioned, this causes erosion, poor heat transfer and also blockages and encrustations.

To avoid these disadvantages of a catalyst circuit, it has been proposed that the catalyst salts be retained in the reactor in suspended form and that methanol, CO and oxygen be metered into the reactor, while the dialkyl carbonate formed and the water of reaction are distilled out of the reactor together with methanol used in excess (EP 0 413 215 A2). The liquid reaction medium here consists essentially of the methanol to be reacted (EP-0 413 215, page 3, line 52), so that the molar ratio of methanol to Cu salt is very high (preferably 1:0.01–0.05). This has the disadvantage that the reaction rate is relatively low. A problem here is also the need to set a low dimethyl carbonate concentration. This is not easy, since the reaction is carried out at a high system pressure and the solubilities of dimethyl carbonate and also of water in the reaction medium, which consists essentially of methanol, are very high. This means that the separating off of dimethyl carbonate and water has to be forced by means of a relatively large amount of inert gas or methanol gas.

In a relatively new process in accordance with German Offenlegungsschrift 41 38 755, it has been shown that the reaction rate for the oxycarbonylation of methanol can be substantially increased if Cu compounds in the form of molten salts at from 120° to 300° C. are used.

The particular advantage of this process becomes valuable when the water content in the reaction mixture can be kept low (Patent Application P 43 25 651.1 of 30.7.1993).

SUMMARY OF THE INVENTION

An improved process has now been found for preparing dimethyl carbonate by reaction of methanol with carbon monoxide and oxygen in the presence of copper compounds, which comprises carrying out the reaction in the presence of molten Cu salts at from 120° C. to 300° C. and from 1 to 70 bar in a reaction distillation unit in such a way that the water of reaction formed during the reaction is separated off at least partially from the stripper region or the bottom phase of this reaction distillation unit.

BRIEF DESCRIPTION OF THE DRAWINGS

The accompanying

DETAILED DESCRIPTION OF THE INVENTION

Figure 1:
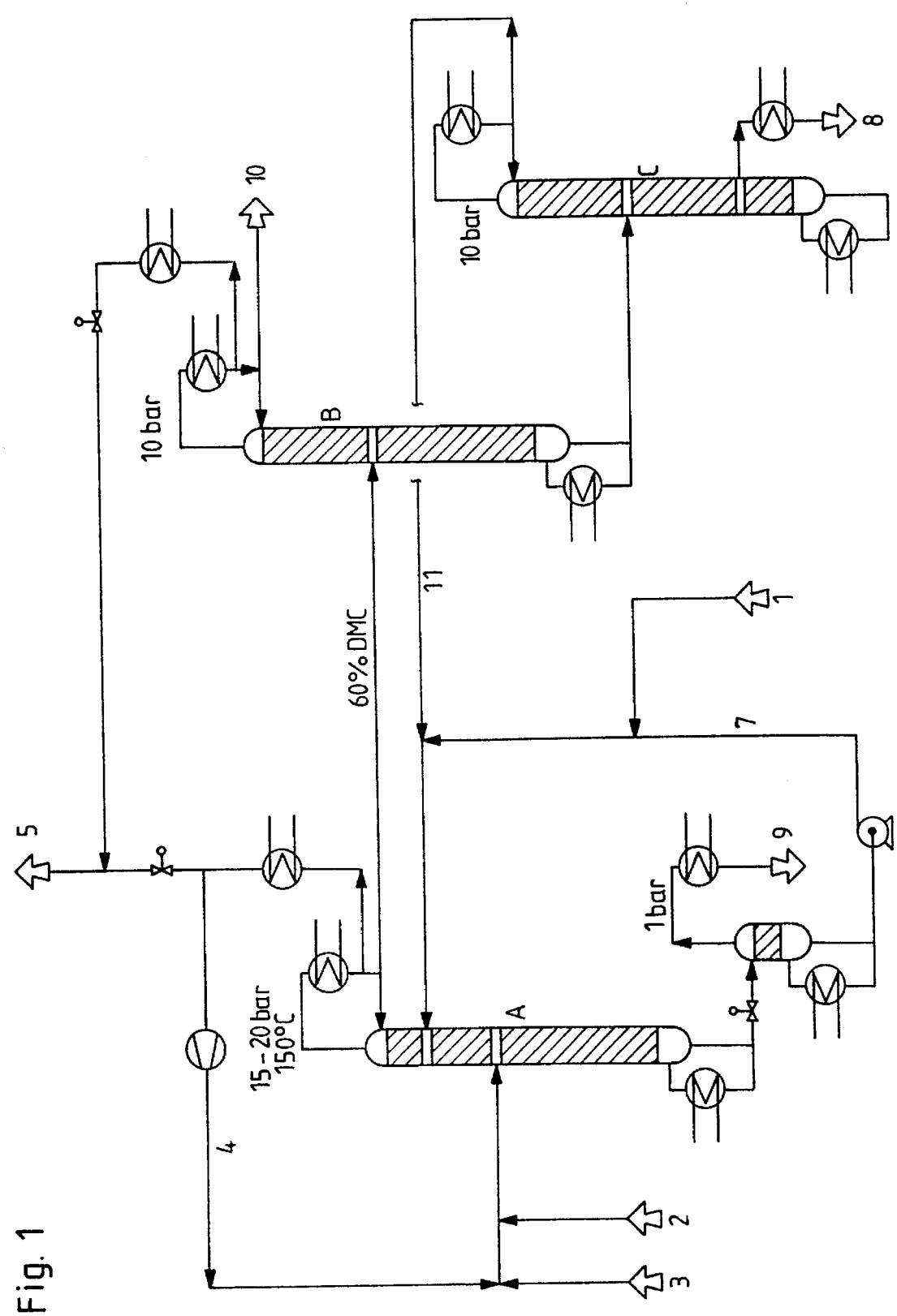
FIGS. 1 and 2 show examples of apparatus arrangements to carry out the present invention.

In this way the water of reaction can be removed from the reaction system and the melt containing Cu salt can, after separating off the water and any organics present, such as dimethyl carbonate, methanol or other species present in the system, be recirculated to the reaction distillation unit.

In this way, the water content of the reaction mixture is controlled and reduced to low values. The process is generally carried out at a water content of below 10%. However, it is advantageous to keep the water concentration below 6% by weight in the reaction mixture. For a high conversion at simultaneously very high selectivities, it is particularly advantageous to operate the reaction at values below 3% by weight. In specific embodiments, the water content is below 1%.

The process of the invention is preferably carried out using a salt melt containing a Cu salt, with suitable Cu salts being Cu(I) and Cu(II) compounds and also mixtures thereof. In principle, all known Cu salts are suitable, provided that they are soluble to only some extent in the salt melt.

Besides the halides such as, for example, the chlorides or the bromides, suitable salts are also the cyanides, rhodanides, sulphates, nitrates, carbonates, acetates, formates, oxalates and alkoxides, e.g. copper methoxychloride.

Cu can also be used in the form of complex compounds, such as the acetyl acetonates, or Cu-N complexes such as Cu-pyridine or also Cu-dipyridyl complexes.

The salt melt is generally made up of mixtures of salts which have a low melting point, i.e. which form a eutectic. It is therefore advantageous to use ratios of the salts corresponding to the composition of the eutectic. Such eutectics can be formed from mixtures of Cu salts with one another or of Cu salts and further salts.

It is therefore possible in principle to use, besides the Cu salts, all salts which are chemically inert or else are catalytically active for the purposes of the present invention, i.e. which reduce the activation energy for the oxycarbonylation of alkanols. Besides Cu salts, use can here be made of a wide range of salts or salt-like compounds. Mixtures of Cu salts and such salt-like compounds are generally used. Preference is given to using the halides of the 1st to 3rd main groups and subgroups. Particularly suitable salts are the chlorides of the alkali metals, such as NaCl or KCl, or chlorides of the alkaline earth metals, such as $CaCl_2$ or $MgCl_2$, and also $ZnCl_2$. However, it is also possible to use less common compounds such as the chlorides of thallium, indium or gallium.

A well-suited melt consists, for example, of Cu(I) chloride and KCl in various ratios. The mixtures generally selected are those having a high proportion of Cu compounds, e.g. in a weight ratio of copper(I) chloride to KCl of 60 to 75:40 to 25.

The reaction temperature is generally from about 120° C. to 300° C., preferably from 120° C. to 180° C.; typical reaction temperatures are from 140° C. to 170° C., advantageously from 145° C. to 160° C.

The reaction can be carried out at atmospheric pressure. However, to achieve a sufficiently high reaction rate, it is advantageous to carry out the reaction at a higher pressure, e.g. at from 5 to 70 bar, preferably at from 10 to 50 bar, particularly preferably at from 12 to 22 bar.

The molar ratios of the reaction components used are important for the reaction rate and for the selectivity of the reaction. If these relationships are not observed, there is formation of by-products such as the dimethyl acetal of formaldehyde or, causing a particular problem, methyl chloride.

The ratios are generally selected so as to use a molar excess of methanol to carbon monoxide and in turn an excess of carbon monoxide to oxygen, but at most molar amounts of CO and $O_2$. Thus, the molar ratios selected of alkanol to CO and $O_2$ are 1:1–0.01:1–0.01, preferably 1:0.5–0.02:0.3–0.02. This results in a methanol conversion of, for example, from 10 to 50% and a CO conversion of from 10 to 80%. Oxygen is generally completely reacted. Of course, it is necessary to take note of the explosive limits in selecting the amounts used. If desired, it is possible to carry out the reaction in the presence of inert gases such as $N_2$ or $CO_2$.

The oxygen can be used, for example, in the form of atmospheric air or of air enriched with $O_2$.

The unreacted amounts of methanol and CO can be recirculated after separating off dimethyl carbonate and $H_2O$, optionally also $CO_2$.

The process of the invention can be carried out batchwise. However, it is particularly suitable for continuous automotive production of dimethyl carbonate. Suitable reaction distillation units are conventional distillation columns in which the melt containing Cu salt is metered in below the top zone and, together with the runback of the column and optionally methanol used, flows downwards over the internal fittings or the packing of the column, with a gas mixture comprising oxygen and CO, optionally in the presence of inert gases such as $N_2$ or $CO_2$, being introduced into the middle region of the column, this gas mixture flowing towards the methanol-containing salt melt.

The residence time of the reaction gases in the melt is generally sufficient in conventional distillation units to achieve sufficient conversion to dimethyl carbonate. In this way, residence times of from 0.5 to 500 seconds can easily be set. If desired, the residence time can be raised further by increasing the amount of liquid phase. Besides the customary packings, use can also be made of the customary column plates. However, it is also possible to set the desired residence time, for example, by raising the downflow weirs in plate columns. The reaction distillation units used can also be single-stage to multistage bubble columns, which may optionally also be stirred.

The liquid flowing down below the entry point of the reaction gases CO and $O_2$ contains, besides the Cu salts, water of reaction and possibly also dimethyl carbonate. Depending on the pressure and temperature conditions and runback ratios, the amount of dimethyl carbonate which flows towards the bottom together with the melt and the water of reaction can be varied or fixed. The conditions in the reaction distillation unit can also be selected in such a way that the DMC formed in the reaction is mostly taken off at the top together with the methanol. However, the conditions can also be selected in such a way that the DMC is taken out at the bottom together with the melt and the water of reaction. The bottom phase is subsequently freed of the water of reaction and, if appropriate, of the DMC, for example depressurization. The melt flows back into the reaction zone, optionally together with the fresh methanol.

The water of reaction is removed from the system, optionally after distilling off organics such as DMC.

In the zone of the reaction distillation unit above the inflow point of the molten salts, methanol and possibly dimethyl carbonate distil off, together with small amounts of volatile by-products such as, for example, formaldehyde dimethylacetal.

The top product is, after condensation, optionally partially recirculated into the reaction distillation unit. The proportion of the condensate not recirculated is taken from the column. Pure DMC is isolated in a known manner from this material taken from the column and the methanol is recirculated to the reaction zone.

The heat of reaction generated in the reaction zone is removed by means of reactants which vaporize.

Any mixtures of methanol and dimethyl carbonate obtained in the work-up of the reaction mixture can be recirculated as mixtures to the reaction zone and serve as a source of methanol.

In this way, methanol introduced into the reaction zone can already contain relatively large amounts of dimethyl carbonate which, for example, have a composition corresponding to the methanol/dimethyl carbonate azeotrope, but can also contain higher amounts of DMC.

The particular advantage of the process of the invention is that the reaction mixtures obtained have high dimethyl carbonate contents, for example from 10 to 90% by weight, preferably from 50 to 70% by weight, which allow isolation of the pure dimethyl carbonate in a particularly simple and economical manner.

Suitable materials of construction for the reaction distillation unit are, for example, corrosion-resistant stainless steels, enamelled steels, glass, graphite or special metals such as tantalum.

The process of the invention can also be carried out industrially on a larger scale. Here, for example as shown in FIG. 1, use can be made of a reaction distillation unit (A) through which methanol (1) together with the salt melt (7) and the DMC/methanol azeotrope (11) are passed in counter-current to a gas stream of CO (2) and $O_2$ (3) together with the circulating gas (4).

From the bottom of the column of the unit (A), the water of reaction (9) is distilled off after depressurization. The melt freed of water is recirculated to the column (A).

At the top of the column (A), after condensation, a substream of the condensed phase is returned to the column. The other substream, which contains about 60% of DMC (remainder: methanol), flows into the azeotrope column (B) from which dimethyl formal (10) is taken off at the top at 10 bar. The bottom discharge from the azeotrope column (B) goes into the dimethyl carbonate purification column (C) from which pure dimethyl carbonate (8) is obtained as a bleed stream in the vicinity of the bottom. The top product of the DMC purification column (C) consists essentially of the azeotrope of dimethyl carbonate and methanol and is recirculated together with the salt melt to the reaction zone.

The non-condensable components (4) from the reaction distillation unit (A) are recirculated to the reaction zone by means of a compressor. A substream of the circulating gas (5) is bled off to remove inert gases.

Figure 2:
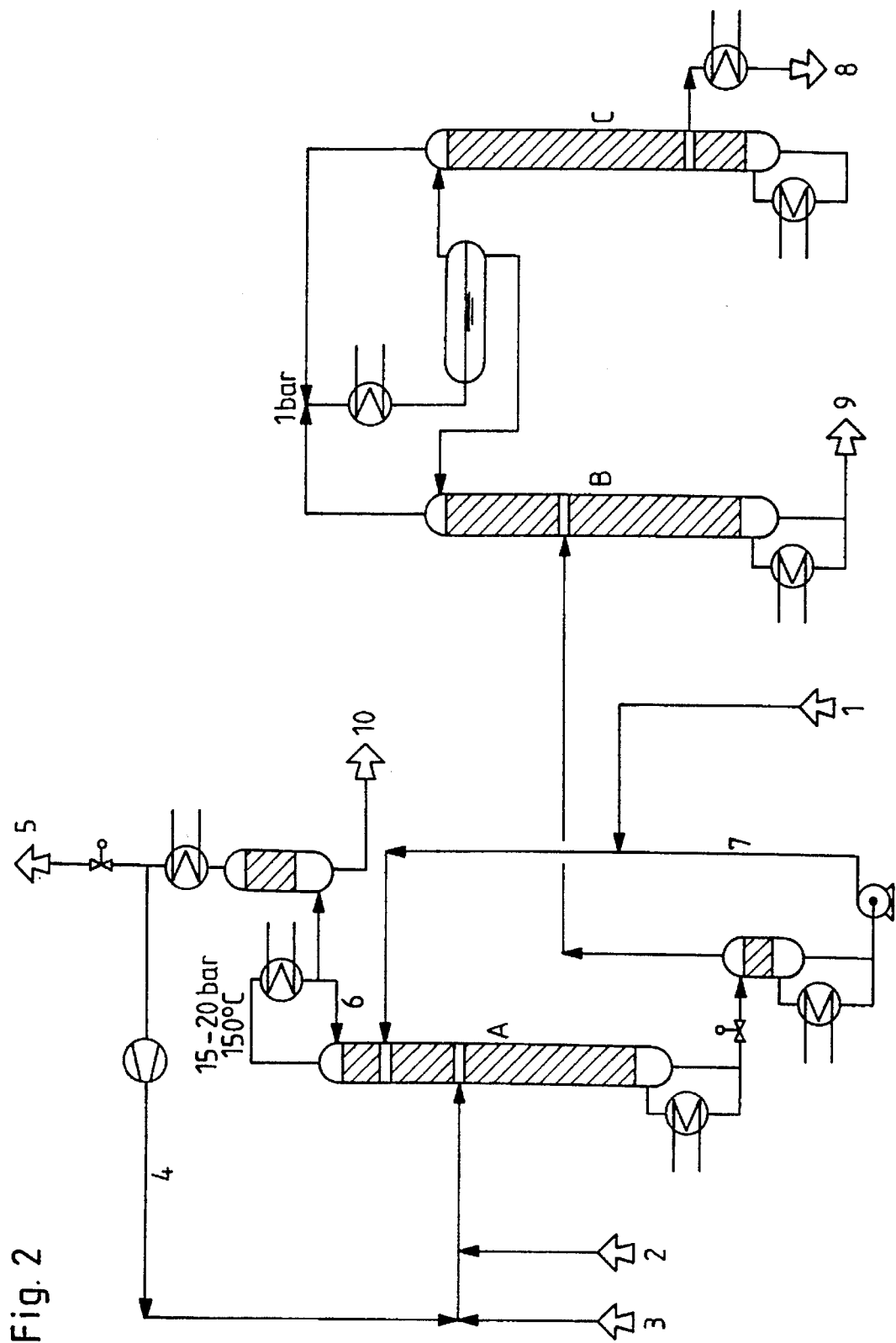

However, it is also possible to carry out the process as shown in FIG. 2 by introducing methanol (1) together with the melt (7) into the reaction distillation unit (A). This stream flows downwards through the interior fittings of the column and the mixture of the reaction gases $O_2$ (3) and CO (2) together with the circulating gas (4) flows upwards in counter-current thereto. Below the reaction zone, a mixture of molten salts, water and dimethyl carbonate flows to the bottom of the reaction distillation column, where this product stream comprising salt melt, water and dimethyl carbonate is taken off. Water and dimethyl carbonate are distilled off from this material drawn off at the bottom and are fractionated in the water separation column (B), where water (9) is obtained at the bottom.

At the top, the water/dimethyl carbonate azeotrope distils off. After phase separation, the water separated off flows back into the column. The organic upper phase essentially contains dimethyl carbonate which is taken off from the DMC purification column (C) as a bleed stream in the vicinity of the bottom (8).

Above the reaction zone of the reaction distillation unit (A), the materials which distil out consist essentially of methanol and volatile by-products such as formaldehyde dimethyl acetal. The condensate is essentially returned as product stream (6) as runback to the reaction distillation column (A). To remove volatile by-products from the system, a substream of the condensate has a smaller substream (purge, 10) bled off. The non-condensable components of the top product (4) are recirculated to the reaction zone by means of a compressor. To remove inert gases, a substream (5) is bled off from this circulating gas.

| Mass balance for the DMC salt-melt process |
|---|

| Example as shown in FIG. 1 | | | | | | | | | | | |
|---|---|---|---|---|---|---|---|---|---|---|---|
| | Methanol Feed 1 | | Carbon monoxide Feed 2 | | Oxygen Feed 3 | | Circulating gas 4 | | Purge 5 | | Return 6 | |
| Methanol | 2931 | 100.0% | | 0.0% | | 0.0% | | 0.0% | | 0.0% | 18016 | 40.0% |
| CO | | 0.0% | 1262 | 100.0% | | 0.0% | 3578 | 40.6% | 23 | 40.6% | | 0.0% |
| $N_2$ | | 0.0% | | 0.0% | | 0.0% | | 0.0% | | 0.0% | | 0.0% |
| $O_2$ | | 0.0% | | 0.0% | 735 | 100.0% | 773 | 8.8% | 5 | 8.8% | | 0.0% |
| DMC | | 0.0% | | 0.0% | | 0.0% | | 0.0% | | 0.0% | 27024 | 60.0% |
| Formal | | 0.0% | | 0.0% | | 0.0% | | 0.0% | | 0.0% | | 0.0% |
| $CO_2$ | | 0.0% | | 0.0% | | 0.0% | 4464 | 50.6% | 29 | 50.6% | | 0.0% |
| CuCl/KCl | | 0.0% | | 0.0% | | 0.0% | | 0.0% | | 0.0% | | 0.0% |
| Water | | 0.0% | | 0.0% | | 0.0% | | 0.0% | | 0.0% | | 0.0% |
| | 2931 | 100.0% | 1262 | 100.0% | 735 | 100.0% | 8814 | 100.0% | 58 | 100.0% | 45040 | 100.0% |

| | Product 8 | | Water of reaction 9 | | Formaldehyde di-methyl acetal (FDA) 10 | | Azeotrope return 11 | |
|---|---|---|---|---|---|---|---|---|
| Methanol | | 0.0% | | 0.0% | | 0.0% | 3023 | 85.0% |
| CO | | 0.0% | | 0.0% | | 0.0% | 0 | 0.0% |
| $N_2$ | | 0.0% | | 0.0% | | 0.0% | 0 | 0.0% |
| $O_2$ | | 0.0% | | 0.0% | | 0.0% | 0 | 0.0% |
| DMC | 4000 | 100.0% | | 0.0% | | 0.0% | 533 | 15.0 |
| Formal | | 0.0% | | 0.0% | 68 | 100.0% | 0 | 0.0 |
| $CO_2$ | | 0.0% | | 0.0% | | 0.0% | 0 | 0.0 |
| CuCl/KCl | | 0.0% | | 0.0% | | 0.0% | 0 | 0.0% |
| Water | | 0.0% | 832 | 100.0% | | 0.0% | 0 | 0.0% |
| | 4000 | 100.0% | 832 | 100.0% | 68 | 100.0% | 3556 | 100.0% |

Example as shown in FIG. 2

-continued

Mass balance for the DMC salt-melt process

|  | Methanol Feed 1 | | Carbon monoxide Feed 2 | | Oxygen Feed 3 | Circulating gas 4 | | Purge 5 | | Return 6 | |
|---|---|---|---|---|---|---|---|---|---|---|---|
| Methanol | 2931 | 100.0% |  | 0.0% |  |  | 0.0% |  | 0.0% | 38284 | 85.0% |
| CO |  | 0.0% | 1262 | 100.0% |  | 3578 | 40.6% | 23 | 40.6% |  | 0.0% |
| N$_2$ |  | 0.0% |  | 0.0% |  |  | 0.0% |  | 0.0% |  | 0.0% |
| O$_2$ |  | 0.0% |  | 0.0% | 735 | 773 | 8.8% | 5 | 8.8% |  | 0.0% |
| DMC |  | 0.0% |  | 0.0% |  |  | 0.0% |  | 0.0% | 6756 | 15.0% |
| Formal |  | 0.0% |  | 0.0% |  |  | 0.0% |  | 0.0% |  | 0.0% |
| CO$_2$ |  | 0.0% |  | 0.0% |  | 4464 | 50.6% | 29 | 50.6% |  | 0.0% |
| CuCl/KCl |  | 0.0% |  | 0.0% |  |  | 0.0% |  | 0.0% |  | 0.0% |
| Water |  | 0.0% |  | 0.0% |  |  | 0.0% |  | 0.0% |  | 0.0% |
|  | 2931 | 100.0% | 1262 | 100.0% | 735 | 8814 | 100.0% | 58 | 100.0% | 45040 | 100.0% |

|  | Product 8 | | Water of reaction 9 | | Formaldehyde dim-ethyl acetal (FDA) 10 | |
|---|---|---|---|---|---|---|
| Methanol |  | 0.0% |  | 0.0% |  | 0.0% |
| CO |  | 0.0% |  | 0.0% |  | 0.0% |
| N$_2$ |  | 0.0% |  | 0.0% |  | 0.0% |
| O$_2$ |  | 0.0% |  | 0.0% |  | 0.0% |
| DMC | 4000 | 100.0% |  | 0.0% |  | 0.0% |
| Formal |  | 0.0% |  | 0.0% | 68 | 100.0% |
| CO$_2$ |  | 0.0% |  | 0.0% |  | 0.0% |
| CuCl/KCl |  | 0.0% |  | 0.0% |  | 0.0% |
| Water |  | 0.0% | 832 | 100.0% |  | 0.0% |
|  | 4000 | 100.0% | 832 | 100.0% | 68 | 100.0% |

What is claimed is:

1. A continuous process for the preparation of dimethyl carbonate wherein liquid methanol, a salt melt containing a Cu salt and a dimethyl carbonate/methanol azeotope are passed countercurrently to carbon monoxide and oxygen gas in a distillation column reactor, the bottoms product of the distillation column is withdrawn, processed to remove water and recycled to the column and the overhead product is condensed and split into two portions, one portion of which is recycled to the top of the distillation column and a second portion which is distilled to remove dimethyl formal and then further distilled to form an overhead product of dimethyl carbonate/methanol azeotope, which is recycled to the distillation column reactor, and a bottoms product of dimethyl carbonate.

2. The process of claim 1, wherein the water content in the reaction medium is maintained at a value of below 10% by weight.

3. The process of claim 2, wherein the water content in the reaction medium is maintained at a value of below 6% by weight.

4. The process of claim 3, wherein the water content in the reaction medium is maintained at a value of below 3% by weight.

5. The process of claim 4, wherein the water content in the reaction medium is maintained at a value of below 1% by weight.

6. The process of claim 1, wherein said salt melt is a melt of Cu(I) chloride and KCl.

7. The process of claim 6, wherein a weight ratio CuCl:KCl=60 to 75:40 to 25 is set.

8. The process of claim 1, wherein a molar ratio of methanol:CO:O$_2$=1:1–0.01:1–0.01 is set.

9. The process of claim 8, wherein a molar ratio of methanol:CO:O$_2$=1:0.5–0.02:0.3–0.02 is set.

* * * * *